United States Patent
Thyresson et al.

(10) Patent No.: US 11,400,047 B2
(45) Date of Patent: Aug. 2, 2022

(54) LOZENGE COMPRISING MICRONIZED BENZOCAINE AND POLYETHYLENE GLYCOL

(71) Applicant: Johnson & Johnson Consumer Inc., Skillman, NJ (US)

(72) Inventors: Kristina Thyresson, Lund (SE); Carina Siversson, Råå (SE); Mikael Bisrat, Strängnäs (SE); Katarina Lindell, Eslöv (SE)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 16/482,421

(22) PCT Filed: Jan. 31, 2018

(86) PCT No.: PCT/US2018/016062
§ 371 (c)(1),
(2) Date: Jul. 31, 2019

(87) PCT Pub. No.: WO2018/144491
PCT Pub. Date: Aug. 9, 2018

(65) Prior Publication Data
US 2019/0358157 A1 Nov. 28, 2019

(30) Foreign Application Priority Data

Feb. 1, 2017 (SE) .................................. 1750079-4

(51) Int. Cl.
*A61K 9/00* (2006.01)
*A61K 31/245* (2006.01)
*A61K 9/20* (2006.01)
*A61K 9/28* (2006.01)

(52) U.S. Cl.
CPC ............ *A61K 9/0056* (2013.01); *A61K 9/205* (2013.01); *A61K 9/2018* (2013.01); *A61K 9/2031* (2013.01); *A61K 9/2866* (2013.01); *A61K 31/245* (2013.01)

(58) Field of Classification Search
CPC ... A61K 9/0056; A61K 9/1641; A61K 9/2031
See application file for complete search history.

(56) References Cited

U.S. PATENT DOCUMENTS

| | | | |
|---|---|---|---|
| 3,511,914 A | 5/1970 | Wolkoff et al. | |
| 5,853,758 A * | 12/1998 | Lo | A61K 9/2095 514/960 |
| 8,569,375 B2 * | 10/2013 | Campbell | A61P 1/00 514/570 |
| 2005/0008704 A1 * | 1/2005 | Ray | A61K 9/2031 514/35 |
| 2005/0152972 A1 | 7/2005 | Singh | |
| 2007/0048369 A1 * | 3/2007 | Foreman | A61K 9/2059 424/464 |
| 2007/0104783 A1 | 5/2007 | Domb et al. | |
| 2009/0004248 A1 * | 1/2009 | Bunick | A61K 9/0056 424/440 |
| 2010/0010101 A1 | 1/2010 | Cherukuri | |
| 2016/0095818 A1 | 4/2016 | Hugerth et al. | |

FOREIGN PATENT DOCUMENTS

| | | |
|---|---|---|
| EP | 2170275 B | 4/2010 |
| WO | WO 2001/019329 A | 3/2001 |

OTHER PUBLICATIONS

SE written opinion and search report dated Aug. 3, 2017, for SE application 1750079-4.
International search report and written opinion dated Apr. 12, 2018, for international application PCT/US2018/016062.
Fitzgerald et al., "Nondestructive Analysis of Tablet Coating Thicknesses Using Terahertz Pulsed Imaging", *Journal of Pharmaceutical Sciences* (2005) 94(1): 177-183.
Hancock et al., "X-ray Microtomography of Solid Dosage forms", *Pharmaceutical Technology* (2005) pp. 92-100.
Kristoffersson et al., "Xylitol as an excipient in oral lozenges", *Acta Pharmaceutica Fenn*, Suomen Farmaseuttinen Yhditys, Helsinki, FI, (1978) 87(2):61-73.
Perez-Ramos et al., "Quantitative Analysis of Film Coating in a Pan Coater Based on In-Line Sensor Measurements", *AAPS Pharm Sci Tech* (2005) 6(1) Article 20:E127-E136.

* cited by examiner

*Primary Examiner* — Lakshmi S Channavajjala

(57) ABSTRACT

The invention relates to a lozenge comprising micronized benzocaine, at least one dissolution enhancer and one or more excipients as well as the use of the lozenge for the treatment of sore throat.

14 Claims, No Drawings

LOZENGE COMPRISING MICRONIZED BENZOCAINE AND POLYETHYLENE GLYCOL

CROSS-REFERENCE TO RELATED APPLICATIONS

This application is the national phase filing under 35 USC 371 of international application PCT/US2018/016062 filed on Jan. 31, 2018, which claims priority to SE 1750079-4 filed on Feb. 1, 2017, the complete disclosures of which are hereby incorporated herein by reference for all purposes.

FIELD OF THE INVENTION

The invention relates to a lozenge comprising micronized Benzocaine, at least one dissolution enhancer and one or more excipients as well as the use of the lozenge for the treatment of sore throat.

BACKGROUND OF THE INVENTION

Sore throat is generally treated using lozenges containing a therapeutically effective amount of an Active Pharmaceutical Ingredient (API). Suitably, the lozenge is dissolved slowly in the mouth and the API released in the oral cavity and delivered to the surface of the sore throat (i.e. mucous membrane).

Benzocaine is a local anesthetic agent commonly used as a topical pain reliever in topical products, cough drops or hard boiled candies. Topically administered Benzocaine is used to reduce pain or discomfort caused by minor skin irritations, sore throat, sunburn, teething pain, vaginal or rectal irritation, ingrown toenails, hemorrhoids, and many other sources of minor pain on a surface of the body. Benzocaine is also used to numb the skin or surfaces topically inside the mouth, nose, throat, vagina, or rectum to lessen the pain of inserting a medical instrument such as a tube or speculum. Benzocaine is the active ingredient in many pharmaceutical over-the-counter products.

EP2170275 relates to a dosage form having both a disintegrative portion and a hard candy portion, wherein the disintegrative portion should dissolve in preferably less than about 15 seconds, which is much too fast to be able to give an effect.

U.S. Pat. No. 3,511,914 relates to a flavored medicated lozenge capable of dissolving slowly and uniformly in the mouth comprising a major amount of polyethylene glycol and having a medicament.

US2005152972 relates to an oral anaesthetic based on a soft chewable lozenge which disintegrates and dissolves slowly in the mouth to sooth an irritated area.

US2016/095818 relates to a solid pharmaceutical dosage form intended for release of one or more Active Pharmaceutical ingredients (API) in the oral cavity, wherein the API is taste masked due to bad taste.

The most efficient Benzocaine products available on the market today for treatment of pain caused by sore throat comprise Benzocaine in hard boiled candy lozenges. Hard boiled candy lozenges are large in size which is not pleasant for most of the consumers. In hard boiled candies Benzocaine resides in the amorphous phase and it will be very fast dissolved thus giving the consumer a fast pain relief. However, imperfections, of the surface of the lozenge caused by incorporation of air bubbles in the viscous melt mass before cooling may damage the mucous membranes in the oral cavity while the lozenge is dissolving.

SUMMARY OF THE INVENTION

The invention relates to a compressed lozenge comprising micronized Benzocaine, at least one dissolution enhancer and one or more excipients.

Benzocaine in the crystalline phase provides a slow dissolution compared to Benzocaine in the amorphous phase. Thus, the problem to be solved was to develop a lozenge comprising Benzocaine in the crystalline phase having about the same dissolution profile as Benzocaine in the amorphous phase, i.e., being bioequivalent with the hard boiled candies comprising Benzocaine in the amorphous phase and present on the market for the treatment of sore throat.

In addition to the same dissolution rate the lozenge should be small, i.e., mouth friendly and give rise to a smooth mouth feeling.

The invented lozenge is suitable for the treatment of sore throat.

The dissolution problem was solved by using micronized Benzocaine together with specific dissolution enhancers that surprisingly showed similar dissolution profiles compared to the amorphous Benzocaine products.

DETAILED DESCRIPTION OF EMBODIMENTS OF THE INVENTION

Definitions

The term "dissolution enhancer" is intended to mean an agent that increases the dissolution of the active ingredient, i.e., benzocaine.

The term "lozenge" means preparations that are solid containing one or more active substances intended for administration to the oral cavity and/or the throat to obtain a local or systemic effect.

Lozenge

In a first aspect, the invention relates to a lozenge, which might be direct compressed or granulated and compressed, comprising micronized Benzocaine, at least one dissolution enhancer and one or more excipients.

The dissolution enhancer may be selected from the group consisting of polyethylene glycol (PEG), sodium dodecylsulphate (SDS) and poloxamer or a mixture thereof. In one example PEG may be used or mixtures of different PEGs. Examples of different PEGs are PEG 4000 to PEG 6000, PEG 6000 or mixtures thereof. The particle size range of PEG may influence the dissolution rate. Different grades of PEG may be used as well.

The micronized Benzocaine present in the lozenge may have a mass median particle size of about 5 to about 30 μm, such as about 7 to about 25 μm, about 7 to about 18 μm, about 10 to about 22 μm, about 12 to about 20 μm, about 14 to about 18 μm.

Benzocaine may be present in an amount of from about 2 to about 15 mg, about 8 to about 15, about 15, 14, 13, 12, 11, 10, 9, 8, 7, 6, 5, 4, 3 or 2 mg per unit dose.

The dissolution enhancers may be present in an amount of from about 1 to about 30 mg, about 4 to about 17 mg per unit dose. When the dissolution enhancer is PEG 6000 it is present in an amount of about 5 to about 25, such as about 10 mg per unit dose.

Examples of excipients include fillers, glidants, lubricants, sweeteners, flavors, coloring agents, binding/gelling agents and mixtures thereof.

Suitable lubricants include long chain fatty acids and their salts, such as magnesium stearate and stearic acid, talc, glycerides waxes, and mixtures thereof.

Suitable glidant is colloidal silicon dioxide.

Examples of sweeteners include, synthetic or natural sugars; artificial sweeteners such as saccharin, sodium saccharin, aspartame, acesulfame, thaumatin, glycyrrhizin, sucralose, cyclamate, dihydrochalcone, alitame, miraculin and monellin; sugar alcohols such as sorbitol, mannitol, glycerol, lactitol, maltitol, and xylitol; sugars extracted from sugar cane and sugar beet (sucrose), dextrose (also called glucose), fructose (also called laevulose), and lactose (also called milk sugar); isomalt, stevia, and mixtures thereof.

Examples of flavoring agents/flavors include, fruit and berry flavors such as lime, orange, lemon, black current, blood orange, cranberry, cloudberry, goji berry, raspberry, strawberry, wild strawberry, sea buckthorn, cherry, melon, kiwi, papaya, pineapple, passion fruit, coconut, and other flavors such as honey, herbs, the, anise, water grass, lemon grass, cooling agent ginger, coffe, eucalyptus, mangostan, peppermint, spearmint, wintergreen, cinnamon, cacao/cocoa, vanilla, liquorice, salt, pepper, chili, menthol, aniseeds, mint or mixtures thereof. The flavoring agents/flavors may be natural extracts as well as synthetic versions.

Examples of coloring agents include lakes and dyes being approved as a food additive.

Examples of fillers that may be used include maltitol, xylitol, sorbitol, mannitol, lactose, dextrose, saccharose or fructose, or any mixture thereof. One example is mannitol.

Examples of biding/gelling agents include but are not limited to xanthan gum, alginate, locust bean gum and guar gum as well as mixtures thereof. One example is xanthan gum.

In one example the filler is mannitol, the binding/gelling agent is xanthan gum and the lubricant is magnesium stearate.

The lozenge may be coated with a film coating agent, such as one or more fil-forming polymers. The thickness of the film coating has an influence on the degree of reduction of the organoleptically disturbing sensations. The film coating may have an average thickness from 10 to 500 microns, more preferably from 20 to 250 microns, such as from 30 to 150 microns. The film thickness may be measured using different methods known in the art such as SEM (Scanning Electron Microscopy), digital micrometer, X-ray microtomography, terahertz pulsed imaging etc. See further e g Quantitative Analysis of Film Coating in a Pan Coater Based on In-Line Sensor Measurements, Jose D. Perez-Ramos et al, AAPS PharmSciTech 2005; 6 (1) Article 20, Nondestructive analysis of tablet coating thicknesses using terahertz pulsed imaging. J Pharm Sci. 2005; 94:177Y183. Fitzgerald A J, Cole B E, Taday P F., Hancock B, Mullarney M P. X-ray microtomography of solid dosage forms. Pharm Technol. 2005; 29:92Y100.

The film-forming polymers may be chosen among cellulose ethers e g hydroxy propyl methyl cellulose (HPMC), methyl hydroxy ethyl cellulose (MHEC), hydroxy propyl cellulose (HPC), hydroxyethyl cellulose (HEC), ethyl hydroxyl ethyl cellulose (EHEC), and other film forming polymers such as methacrylic acid copolymer-type C sodium carboxy methyl cellulose, polydextrose, polyethylene glycols, acrylate polymers (e g poly vinyl acrylate (PVA)), polyvinyl alcohol-polyethylene glycol graft copolymers, complex of polyvinylpyrrolidone (PVP), such as povidone, polyvinyl alcohol, microcrystalline cellulose, carrageenan, pregelatinized starch, polyethylene glycol, and combinations thereof. Typically, the molecular weight (weight average and/or number average) of the polymer is from 1,000 to 10,000,000, preferably from 10,000 to 1,000,000, as measured by e.g. gel permeation chromatography. In one embodiment the film-forming polymers are selected among cellulose ethers e g hydroxy propyl methyl cellulose (HPMC), methyl hydroxy ethyl cellulose (MHEC), hydroxy propyl cellulose (HPC), hydroxyethyl cellulose (HEC), ethyl hydroxyl ethyl cellulose (EHEC).

In addition the film coating may contain one or more plasticizer may be added to the film-forming polymer to facilitate the spreading and film forming capability. Examples on useful plasticizers are glycerol, propylene glycol, polyethylene glycol (PEG 200-6000), organic esters e g triacetin (glyceryl triacetate), triethyl citrate, diethyl phtalate, dibutyl phtalate, dibutyl sebacete, acetyltriethyl citrate, acethyltributyl citrate, tributyl citrate, and oils/glycerides such as fractionated coconut oil, castor oil and distilled acetylated monoglycerides. Additionally, or alternatively, surfactants may be included to facilitate the incorporation of flavors and to improve penetration and spreading properties of the coating liquid. Non-limiting examples of surfactant are polysorbates derived from PEGylated sorbitan esterified with fatty acids such as Polysorbate 20 (Polyoxyethylene (20) sorbitan monolaurate), Polysorbate 40 (Polyoxyethylene (20) sorbitan monopalmitate), Polysorbate 60 (Polyoxyethylene (20) sorbitan monostearate), Polysorbate 80 (Polyoxyethylene (20) sorbitan monooleate) (e g Tween 80, Tween 40, Tween 20), sodium lauryl sulphate (SLS), poloxamer surfactants i.e. surfactants based on ethylene oxide-propylene oxide block copolymers and other surfactants with high HLB-value.

Other components may be included in the composition of the film such as coloring agents, opacifiers, glossing agents, pore forming agents, excipient stabilizers.

The dosage forms of the invention may be prepared by way of a variety of routine techniques, and using standard equipment, known to the skilled person (see, for example, Lachman et al, "The Theory and Practice of Industrial Pharmacy", Lea & Febiger, 3.sup.rd edition (1986) and "Remington: The Science and Practice of Pharmacy", Gennaro (ed.), Philadelphia College of Pharmacy & Sciences, 19.sup.th edition (1995)). In one embodiment, a core comprising Benzocaine is first produced using known tableting techniques, which is then coated with a solution containing a film-forming polymer.

Standard mixing equipment may be used for mixing together components of compositions of the invention. The mixing time period is likely to vary according to the equipment used, and the skilled person will have no difficulty in determining by routine experimentation a suitable mixing time for a given combination of ingredient(s). One way of producing the lozenges is found in the examples. The manufacturing process may as well comprise additional steps of granulation, drying and milling and/or sieving to obtain a lozenge.

Use of the Lozenge

In a final aspect the invention relates to the use of the lozenge for the treatment of sore throat.

EXAMPLES

Example 1

Production of the Core

All ingredients were purchased in pharmaceutical quality except for the flavoring agents that were of food grade.

The ingredients shown in table 1 were sieved through a 1 mm mesh and blended.

The blending times were optimized to obtain a homogenous powder mixture obvious for a person skilled in the art.

The lozenges were produced by direct compression of the powder mix.

The lozenge shape was oblong with targeted lozenge weight of 600 mg.

The manufacturing was performed in manufacturing area with controlled temperature and humidity.

Table 1 and 2 shows the amounts of the different ingredients present in the core of the lozenges.

TABLE 1

| Ingredients | Amount mg/lozenge |
|---|---|
| Benzocaine | 15.0 |
| Mannitol | 533.5 |
| Xanthan gum | 12.0 |
| PEG 6000 | 10.0 |
| Poloxamer | 4.0 |
| SDS | 2.0 |
| Magnesiumstearate | 12.0 |
| Mint flavour | 10.00 |
| Sucralose | 1.00 |
| Acesulfame K | 0.50 |

TABLE 2

| Ingredients | Amount mg/lozenge |
|---|---|
| Benzocaine | 15.0 |
| Mannitol | 537.5 |
| Xanthan gum | 12.0 |
| PEG 4000 | 12.0 |
| Magnesiumstearate | 12.0 |
| Mint flavour | 10.00 |
| Sucralose | 1.00 |
| Acesulfame K | 0.50 |

Example 2

Coating of the Lozenge

All ingredients were purchased in pharmaceutical quality except for the flavoring agents that were of food grade.

The lozenges produced in Example 1 were film coated according to the method disclosed below.

The coating polymer was dispersed in warm water and then cooled down. The other raw materials were added into the coating solution.

The coating solution was homogenized.

The cores were then spray coated and the spray coating was controlled on the outlet air temperature of 45° C.

Table 3 shows the ingredients and the amount of a film coating that could be used for specific embodiments of the invention.

TABLE 3

| Ingredients | Amount/lozenge (mg) |
|---|---|
| HPMC | 16.8 |
| Titanium dioxide | 2.5 |
| Mint flavour | 2.5 |
| PEG 400 | 1.5 |
| Sucralose | 0.8 |
| Acesulfame K | 0.4 |
| Polysorbate | 0.1 |
| Aqua purificata | q.s |

Example 3

The dissolution rate was analyzed using the method USP paddle 2 using Liquid Chromatography (LC).

Example: Dissolution Profiles

% Benzocaine dissolved for lozenges with different mass median particle size range of PEG 6000 at given dissolution times

| Dissolution time (min) | No PEG | Standard PEG 10 mg | Fine Powder PEG 10 mg |
|---|---|---|---|
| 3 | 4.7 | 3.9 | 16.4 |
| 5 | 20.7 | 24.2 | 30.9 |

% Benzocaine dissolved for lozenges with different amounts of PEG 6000 at given dissolution times

| Dissolution time (min) | 0 mg PEG | 5 mg PEG | 10 mg PEG | 60 mg PEG |
|---|---|---|---|---|
| 3 | 4.7 | 14.3 | 17.5 | 11.4 |
| 5 | 20.7 | 37.2 | 41.1 | 30.9 |
| 10 | 54.3 | 72.3 | 74.4 | 62.8 |

% Benzocaine dissolved for lozenges with different mass median particle size of Benzocaine at given dissolution times

| Dissolution time (min) | *≤207 μm | *≤7 | *≤3 |
|---|---|---|---|
| 10 | 25.7 | 44.8 | 38.5 |
| 15 | 43.1 | 80.0 | 63.4 |
| 20 | 53.3 | 85.6 | 79.0 |

*Mass median particle size

Example 4: Products for Comparison

| Dissolution time (min) | Anaesthesin 8 mg | Neo Angin 8 mg | Lozenge produced according to Example 1* |
|---|---|---|---|
| 5 | 15.4 | 34.5 | 41.1 |
| 10 | 31.4 | 64.5 | 74.4 |
| 15 | 45.0 | 85.3 | 90.6 |

*The lozenge produced according to Example 1 having 8 mg of Benzocaine.

The invention claimed is:
1. A lozenge comprising:
   a. micronized Benzocaine having a mass median particle size of 7 μm to 18 μm;
   b. at least one dissolution enhancer comprising a PEG; and
   c. one or more excipients,
   wherein the PEG is polyethylene glycol 4000 to 6000 present in an amount from about 1 to about 30 mg.

2. The lozenge according to claim 1, wherein benzocaine is present in an amount from about 2 to about 15 mg.

3. The lozenge according to claim 1, wherein the dissolution enhancer is present in an amount of about 5 to about 25 mg.

4. The lozenge according to claim 1, wherein the excipient is at least one sweetening agent.

5. The lozenge according to claim 4, wherein the sweetening agent is selected from the group consisting of synthetic or natural sugars; saccharin, sodium saccharin, aspartame, acesulfame, thaumatin, glycyrrhizin, sucralose, cyclamate, dihydrochalcone, alitame, miraculin and monellin; sorbitol, mannitol, glycerol, lactitol, maltitol, and xylitol; sucrose, dextrose, fructose and lactose; isomalt, stevia, and mixtures thereof.

6. The lozenge according to claim 1, wherein the excipient is at least one flavoring agent.

7. The lozenge according to claim 6, wherein the flavoring agent is selected from the group consisting of as lime, orange, lemon, black current, blood orange, cranberry, cloudberry, goji berry, raspberry, strawberry, wild strawberry, sea buckthorn, cherry, melon, kiwi, papaya, pineapple, passion fruit, coconut, and other flavors such as honey, herbs, tea, anise, water grass, lemon grass, cooling agent ginger, coffe, eucalyptus, mangosten, peppermint, spearmint, wintergreen, cinnamon, cacao/cocoa, vanilla, liquorice, salt, pepper, chili, menthol, aniseeds, mint, natural or synthetic versions and mixtures thereof.

8. The lozenge according to claim 1, comprising at least one selected from the following excipients; a filler, binding/gelling agent and a lubricant.

9. The lozenge according to claim 8, wherein the filler is mannitol, the binding/gelling agent is xanthan gum, and the lubricant is magnesium stearate.

10. The lozenge according to claim 1, wherein said lozenge is coated with a film forming agent.

11. The lozenge according to claim 10, wherein the film forming agents is a cellulose ether film forming agent.

12. The lozenge according to claim 11, wherein the cellulose ether film forming agent is selected from the group consisting of hydroxy propyl methyl cellulose (HPMC), methyl hydroxy ethyl cellulose (MHEC), hydroxy propyl cellulose (HPC), hydroxyethyl cellulose (HEC), or ethyl hydroxyl ethyl cellulose (EHEC).

13. The lozenge according to claim 1, wherein the lozenge is direct compressed or granulated and compressed.

14. A method of treating a sore throat said method comprising administering a lozenge according to claim 1.

\* \* \* \* \*